US006582911B1

(12) United States Patent
Bussey et al.

(10) Patent No.: US 6,582,911 B1
(45) Date of Patent: Jun. 24, 2003

(54) CANDIDA ALBICANS KRE9 AND USES THEREOF

(75) Inventors: Howard Bussey, Westmount (CA); Marc Lussier, Montréal (CA); Anne-Marie Sdicu, Pierrefonds (CA); Sarkis Serge Shahinian, Montréal (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/581,130

(22) PCT Filed: Dec. 10, 1998

(86) PCT No.: PCT/CA98/01151

§ 371 (c)(1),
(2), (4) Date: Aug. 10, 2000

(87) PCT Pub. No.: WO99/31269

PCT Pub. Date: Jun. 24, 1999

(30) Foreign Application Priority Data

Dec. 12, 1997 (CA) .............................................. 2218446

(51) Int. Cl.[7] .......................... C12Q 1/68; C07H 21/04; C07H 21/00; C07H 5/04; C07H 5/06
(52) U.S. Cl. .......................... 435/6; 435/69.1; 435/193; 435/252.3; 435/254.1; 435/320.1; 536/22.1; 536/23.1; 536/23.2; 536/23.7; 536/23.74; 530/387.1; 424/184.1; 424/185.1; 424/274.1; 514/2; 514/15
(58) Field of Search .......................... 424/184.1, 185.1, 424/274.1; 514/15, 2; 536/22.1, 23.1, 23.2, 23.7, 23.74; 530/387.1; 435/6, 69.1, 193, 252.3, 254.1, 320.1

(56) References Cited

U.S. PATENT DOCUMENTS 5,194,600 A    3/1993   Bussey et al.
5,821,038 A   10/1998   Fleer et al.
5,821,353 A   10/1998   Douglas et al.
5,939,306 A    8/1999   Alex et al.
6,046,000 A    4/2000   McCarthy et al.

FOREIGN PATENT DOCUMENTS

WO    WO 95/32982    12/1995

OTHER PUBLICATIONS

Bork (Genome Research, 2000; 10, 398–400).*
Mio et al., 1997, Journal of Bacteriology, 179:2363–2372.
Montijn et al., 1994, The Journal of Biological Chemistry, 269 :19338–19342.
Brown et al., 1993, Molecular and Cellular Biology, 13:6346–6356.
Boone et al., 1991, Journal of Bacteriology, 173:6859–6864.
Dijkgraaf et al., 1996, Yeast, 12 :683–692.
Roemer et al., 1991, Proc. Natl. Acad. Sci., 88:11295–11299.
Lussier et al., 1998, Proc. Natl. Acad. Sci., 95 :9825–9830.

* cited by examiner

Primary Examiner—Lynette R. F. Smith
Assistant Examiner—Padmavathi Baskar
(74) Attorney, Agent, or Firm—Ogilvi Renault; France Cote

(57) ABSTRACT

The present invention to an isolated DNA which codes for a gene essential for cell wall glucan synthesis of *Candida albicans*, wherein the gene is referred to as CaKRE9, wherein the sequence of the DNA is as set forth in FIG. 1. The present invention relates to antifungal in vitro and in vivo screening assays for identifying compounds which inhabit the synthesis, assembly and/or regulation of β1,6-glucan. There is also disclosed an in vitro method for the diagnosis of disease caused by fungal infection in a patient.

13 Claims, 8 Drawing Sheets

```
      Met Arg Gln Phe Gln Ile Ile Leu Ile Ser Leu Val Val Ser Ile Ile Arg    17
  1   ATG AGA CAA TTT CAA ATC ATA TTA ATT TCC CTT GTT GTT TCC ATA ATA AGA
      Cys Val Val Ala Asp Val Asp Ile Thr Ser Pro Lys Ser Gly Glu Thr Phe    34
 52   TGT GTT GTT GCA GAT GTT GAC ATC ACA TCA CCA AAG AGT GGA GAA ACT TTT
      Ser Gly Ser Ser Gly Ser Ala Ser Ile Lys Ile Thr Trp Asp Asp Ser Asp    51
103   TCT GGT AGT TCT GGA TCA GCA AGT ATC AAG ATT ACC TGG GAT GAT TCA GAC
      Asp Ser Asp Ser Pro Lys Ser Leu Asp Asn Ala Lys Gly Tyr Thr Ile Ser    68
154   GAT TCA GAC TCA CCG AAA TCT TTG GAT AAT GCC AAA GGG TAC ACA ATT TCT
      Leu Cys Thr Gly Pro Thr Ser Asp Gly Asp Ile Gln Cys Leu Asp Pro Leu    85
205   TTA TGT ACT GGA CCT ACT TCA GAT GGG GAT ATC CAG TGT TTG GAT CCA TTA
      Val Lys Asn Glu Ala Ile Ala Gly Lys Ser Lys Thr Val Ser Ile Pro Gln   102
256   GTC AAG AAC GAA GCT ATT GCA GGT AAA TCT AAA ACA GTT TCT ATT CCC CAG
      Asn Ser Val Pro Asn Gly Tyr Tyr Tyr Tyr Phe Gln Ile Tyr Val Thr Thr   119
307   AAC TCA GTA CCT AAT GGT TAT TAC TAT TAT TTC CAA ATT TAC GTT ACT ACT
      Asn Gly Gly Thr Thr Ile His Tyr Ser Pro Arg Phe Lys Leu Thr Gly Met   136
358   AAT GGA GGT ACC ACT ATT CAT TAT TCA CCA CGT TTC AAA TTG ACT GGT ATG
```

```
       Ser Gly Pro Thr Ala Thr Leu Asp Val Thr Glu Thr Gly Ser Val Pro Ala      153
409    TCT GGT CCA ACT GCC ACT TTA GAT GTC ACC GAA ACA GGA TCG GTG CCA GCG
       Asp Gln Ala Ser Gly Phe Asp Thr Ala Thr Ala Asp Ser Lys Ser Phe           170
460    GAT CAA GCT TCA GGA TTT GAT ACT GCA ACT GCC GAC TCC AAA TCT TTC
       Thr Val Pro Tyr Thr Leu Gln Thr Lys Gly Thr Tyr Arg Tyr Ala Pro Met Gln   187
511    ACA GTT CCA TAT ACC CTA CAA ACA AAG GGG ACC TAC AGA CCA ATG CAA
       Met Gln Pro Gly Thr Lys Val Thr Ala Thr Thr Ala Thr Trp Ser Met Lys Phe Pro  204
562    ATG CAA CCA GGT ACC AAA GTG ACT GCT ACA ACC TGG AGT ATG AAG TTC CCA
       Thr Ser Ala Val Thr Tyr Tyr Ser Thr Lys Ala Gly Thr Pro Asn Val Ala      221
613    ACT AGT GCT GTT ACT TAC TAC TCA ACA AAG GCT GGC ACA CCA AAT GTG GCC
       Ser Thr Ile Pro Thr Ile Thr Pro Gly Trp Ser Tyr Thr Ala Glu Ser Ala Val Asn Tyr  238
664    TCT ACT ATT ACC ATT ACC CCA GGT TGG AGT TAT ACT GCT GAA TCT GCC GTT AAC TAT
       Ala Ser Val Ala Pro Tyr Pro Thr Tyr Trp Pro Ala Ser Glu Arg Val           255
715    GCT AGT GTT GCT CCA TAT CCT ACA TAC TGG CCT GCC AGT GAA CGA GTG
       Ser Lys Ala Thr Ile Ser Ala Ala Thr Lys Arg Arg Arg Trp Leu Asp           271
766    AGT AAG GCT ACA ATT AGT GCT GCT ACA AAG AGA AGA AGA TGG TTG GAT TGA
```

```
                    10        20        30        40        50        60
                    |    .    |    .    |    .    |    .    |    .    |
CaKre9p             MRQFQ-IILISLVVSIIRCVVADVDITSPKSGETFSGSSGSASI-KITWDDSDSDSPKSLDN
Kre9p               MRLQR-NSIICALVFLVSFVLGDVNIVSPSSKATFSPSGGTVSV-PVEWMDNGAYPS---LSK
Knh1p               MLIVLFLTLFCSVVFRTAYC--DVAIVAPEPNSVYDLSGTSQAVVKVKWMHTDNTPQEKDFVR 70        80        90        100       110       120
                    |    .    |    .    |    .    |    .    |    .    |
CaKre9p             AKGYTISLCTGPTSDGDIQCLDPL---VKNEAIAGKSK----TVSIPQNSVPNGYYYFQIYVT
Kre9p               ISTFTFSLCTGP--NNNIDCVAVLASKITPSELTQDDKVYSYTAEFASTLIGNGQYYIQVFAQ
Knh1p               ---YTFTLCSG--TNAMIEAMATLQT-LSASDLTDNE----FNAIIENTVGTDGVYFIQVFAQ 130       140       150       160       170       180
                    |    .    |    .    |    .    |    .    |    .    |
CaKre9p             FTNGGTTIHYSPRFKLTGMSGPTATLDVTETGSVPADQASGFDT----ATTADSKSFTVPYTL
Kre9p               VDGQGYTIHYTPRFQLTSMGGVTAYTYSATTEPTPQTSIQTTTTNNAQATTIDSRSFTVPYTK
Knh1p               -TAIGYTIHYTNRFKLKGMIGTKA---ANPSMITIAPEAQTRITTGDVGATIDSKSFTVPYNL

FIG. 2A
```

```
                190       200       210       220       230       240       250
                  |....|....|....|....|....|....|....|....|....|....|....|....|....|
CaKre9p           QTGKTRYAPMQMQPGTKVTATTWSMKFPTSAVTYYSTKAGTPNVASTITPGWSYTAESAVNYA
Kre9p             QTGTSRFAPMQMQPNTKVTATTWTRKFATSAVTYYSTFGSLPEQATTITPGWSYTISSGVNYA
Knh1p             QTGVVKYAPMQLQPATKVTAKTWKRKYATSEVTYYTLRNSVDQHTTVTPGWSYIITADSNYA 260       270       280
                  |....|....|....|....|....|....
CaKre9p           SVAPYPTY--WYPASERVSKATISAATKRRRWLD
Kre9p             TPASMPSDNGGWYKPSKRLSLS---ARKINMRKV
Knh1p             T-APMPADNGGWYNPRKKRLSLTARKVNALRHR
```

FIG. 2B

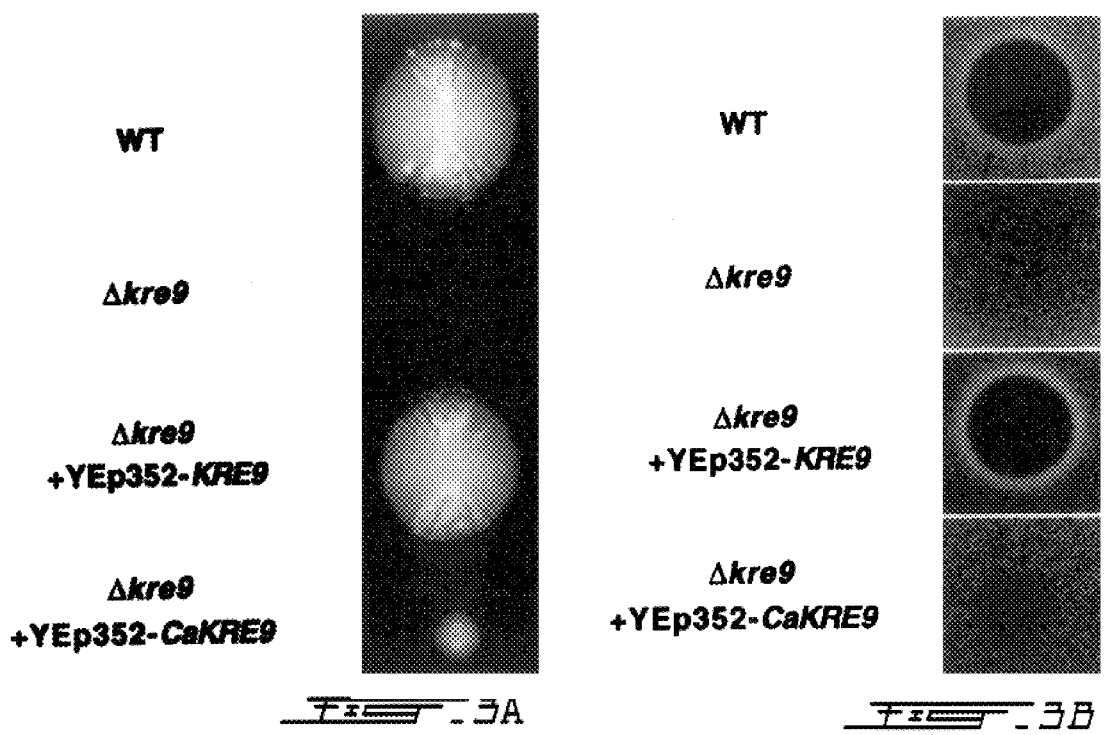

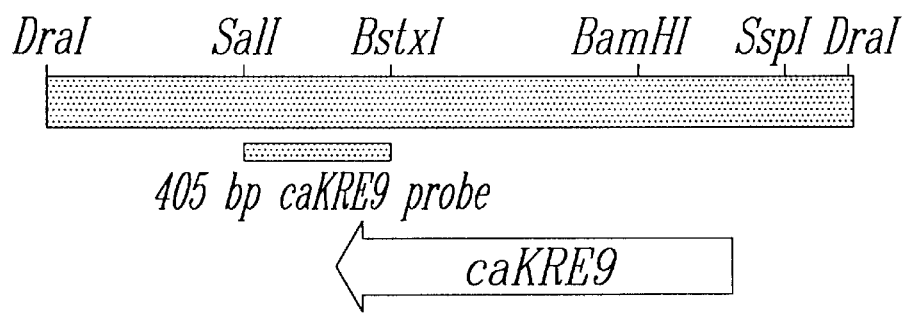
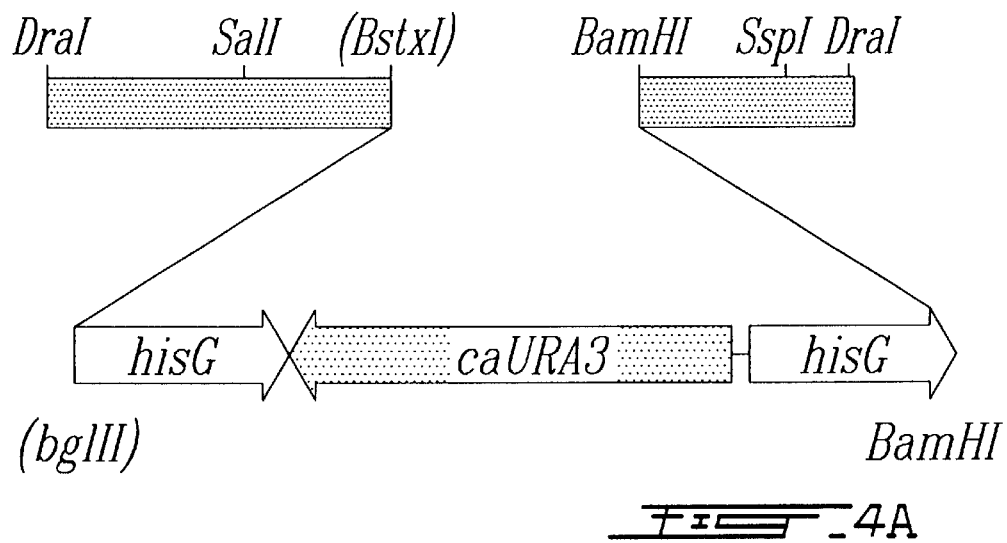
FIG. 4A 1, 2: Wild type 3, 4: *CaKRE9*
       *Cakre9::hisG*

5, 6: *Cakre9::hisG*
       *Cakre9::hisG-URA3-hisG*

CANDIDA ALBICANS KRE9 AND USES THEREOF

BACKGROUND OF THE INVENTION (a) Field of the Invention

The invention relates to a novel gene, CaKRE9, isolated in the yeast pathogen, *Candida albicans*, that is a functional homolog of the *S. cerevisiae* KRE9 gene and which is essential for cell wall glucan synthesis, and to novel antifungal screening assays.

(b) Description of Prior Art

Fungi constitute a vital part of our ecosystem but once they penetrate the human body and start spreading they cause infections or "mycosis" and they can pose a serious threat to human health. Fungal is infections have dramatically increased in the last 2 decades with the development of more sophisticated medical interventions and are becoming a significant cause of morbidity and mortality. Infections due to pathogenic fungi are frequently acquired by debilitated patients with depressed cell-mediated immunity such as those with human immunodeficiency virus (HIV) and now also constitute a common complication of many medical and surgical therapies. Risk factors that predispose individuals to the development of mycosis include neutropenia, use of immunosuppressive agents at the time of organ transplants, intensive chemotherapy and irradiation for hematopoietic malignancies or solid tumors, use of corticosteroids, extensive surgery and prosthetic devices, indwelling venous catheters, hyperalimentation and intravenous drug use, and when the delicate balance of the normal flora is altered through antimicrobial therapy.

The yeast genus Candida constitutes one of the major groups that cause systemic fungal infections and the five medically relevant species which are most often recovered from patients are *C. albicans, C. tropicalis, C. glabrata, C. parapsilosis* and *C. krusei*.

Much of the structure of fungal and animal cells along with their physiology and metabolism is highly conserved. This conservation in cellular function has made it difficult to find agents that selectively discriminate between pathogenic fungi and their human hosts, in the way that antibiotics do between bacteria and man. Because of this, the common antifungal drugs, like amphotericin B and the azole-based compounds are often of limited efficacy and are frequently highly toxic. In spite of these drawbacks, early initiation of antifungal therapy is crucial in increasing the survival rate of patients with disseminated candidiasis. Moreover, resistance to antifungal drugs is becoming more and more prominent. For example, 6 years after the introduction of fluconazole, an alarming proportion of Candida strains isolated from infected patients have been found to be resistant to this drug and this is especially the case with vaginal infections. There is thus, a real and urgent need for specific antifungal drugs to treat mycosis.

The Fungal Cell Wall: a Resource for New Antifungal Targets

In recent years, we have focused our attention on the fungal extracellular matrix, where the cell wall constitutes an essential, fungi-specific organelle that is absent from human/mammalian cells, and hence offers an excellent potential target for specific antifungal antibiotics. The cell wall of fungi is essential not only in maintaining the osmotic integrity of the fungal cell but also in cell growth, division and morphology.

The cell wall contains a range of polysaccharide polymers, including chitin, β-glucans and O- and N-linked mannose sidechains of glycoproteins. β-glucans, homopolymers of glucose, are the main structural component of the yeast cell wall, and constitute up to 60% of the dry weight of the cell wall. Based on their chemical linkage, two different types of polymers can be found: β1,3-glucan and β1,6-glucan. The β1,3-glucan is the most abundant component of the cell wall and it contains on average 1500 glucose residues per molecule. It is mainly a linear molecule but contains some 1,6-linked branchpoints. The β1,6-glucan is a smaller and highly branched molecule comprised largely of 1,6-linked glucose residues with a small proportion of 1,3-linked residues. The average size of β1,6-glucan is approximately 400 residues per molecule. The β1,6-glucan polymer is essential for cell viability as it acts as the "glue" covalently linking glycoproteins and the cell wall polymers β1,3-glucan and chitin together in a crosslinked extracellular matrix.

It would be highly desirable to be provided with the identification and subsequent validation of new cell wall related targets that can be used in specific enzymatic and cellular assays leading to the discovery of new clinically useful antifungal compounds.

SUMMARY OF THE INVENTION

One aim of the present invention is to provide the identification and subsequent validation of a new target that can be used in specific enzymatic and cellular assays leading to the discovery of new clinically useful antifungal compounds.

Although a gene involved in the cellular growth of *S. cerevisiae* was identified, there are no certainties that there would be a homolog in *Candida albicans* or if present that it would have the same function.

In accordance with the present invention a gene was isolated, CaKRE9, in the yeast pathogen, *Candida albicans*, that is a functional homolog of the *S. cerevisiae* KRE9 gene and which is essential for cell wall glucan synthesis. The gene is not found in humans and when it is inactivated in *C. albicans*, the cell cannot survive when grown on glucose, thus, validating it as a wholly new target for antifungal drug discovery.

Using the gene of the present invention, we intend to utilize novel drug screening assays for which we possess all the genetic tools.

In accordance with the present invention there is provided an isolated DNA which codes for a gene essential for cell wall glucan synthesis of *Candida albicans*, wherein the gene is referred to as CaKRE9, wherein the sequence of the DNA is as set forth in FIG. 1.

In accordance with the present invention there is also provided an antifungal screening assay for identifying a compound which inhibits the synthesis, assembly and/or regulation of β1,6-glucan, which comprises the steps of:

a) synthesizing β1,6-glucans in vitro from activated sugar monomer/polymer and specific β1,6-glucan synthetic proteins;

b) subjecting step a) to a high throughput compound screen determining absence or presence of β1,6-glucan, wherein absence of β1,6-glucan is indicative of an antifungal compound.

In accordance with the present invention there is also provided an in vivo antifungal screening assay for identifying compounds which inhibit the synthesis, assembly and/or regulation of β1,6-glucan, which comprises the steps of:

a) separately cultivating a mutant yeast strain lacking one gene for synthesis of β1,6-glucans and a wild type yeast strain with activated sugar monomer/polymer UDP-glucose;

b) subjecting both yeast strains of step a) to the screened compound and determining if the compound selectively inhibits growth of wild type strain which is indicative of an antifungal compound.

In accordance with the present invention there is also provided an in vitro method for the diagnosis of diseases caused by fungal infection in a patient, which comprises the steps of:

a) obtaining a biological sample from the patient;

b) subjecting the sample to PCR using a primer pair specific for CaKRE9 gene, wherein a presence of the gene is indicative of the presence of fungal infection.

In accordance with the present invention, the gene is CaKRE9.

In accordance with the present invention there is also provided an in vitro method for the diagnosis of diseases caused by fungal infection in a patient, which comprises the steps of:

a) obtaining a biological sample from the patient;

b) subjecting the sample to an antibody specific for CaKre9p antigen, wherein a presence of the antigen is indicative of the presence of fungal infection.

In accordance with one embodiment of the present invention, the fungal infection may be caused by Candida.

In accordance with the present invention there is also provided the use of at least one of KRE9 and CaKre9 nucleic acid sequences and fragments thereof as a probe for the isolation of KRE9 homologs in all fungi.

For the purpose of the present invention the following terms are defined below.

The term a "mutant yeast strain" is intended to mean any yeast strain lacking one gene for synthesis of β1,6-glucan, such as KRE9 and homologs thereof.

The term a "wild type yeast strain" is intended to mean any yeast strain containing the KRE9 gene or a homolog thereof or a plasmid overexpressing the KRE9 gene or a homolog thereof.

BRIEF DESCRIPTION OF THE DRAWINGS

FIG. 1 illustrates the complete nucleotide and predicted amino acid sequence of CaKRE9 (SEQ ID NO:1–2).

FIG. 2 illustrates the comparison of the sequence of Kre9p from *Candida albicans* (SEQ ID NO:2) and Kre9p (SEQ ID NO:3) and Knh1p (SEQ ID NO:4) from *Saccharomyces cerevisiae*;

FIG. 3 illustrates the CaKRE9-dependent effect on the growth (A) and Killer phenotype (B) of kre9Δ null mutants;

FIG. 4A illustrates the schematic representation of the strategy for disruption of the *Candida albicans* KRE9 gene;

FIG. 5 illustrates the quantification of β1,6-Glucan levels of different *Candida albicans* strains.

DETAILED DESCRIPTION OF THE INVENTION

Figure 4B:
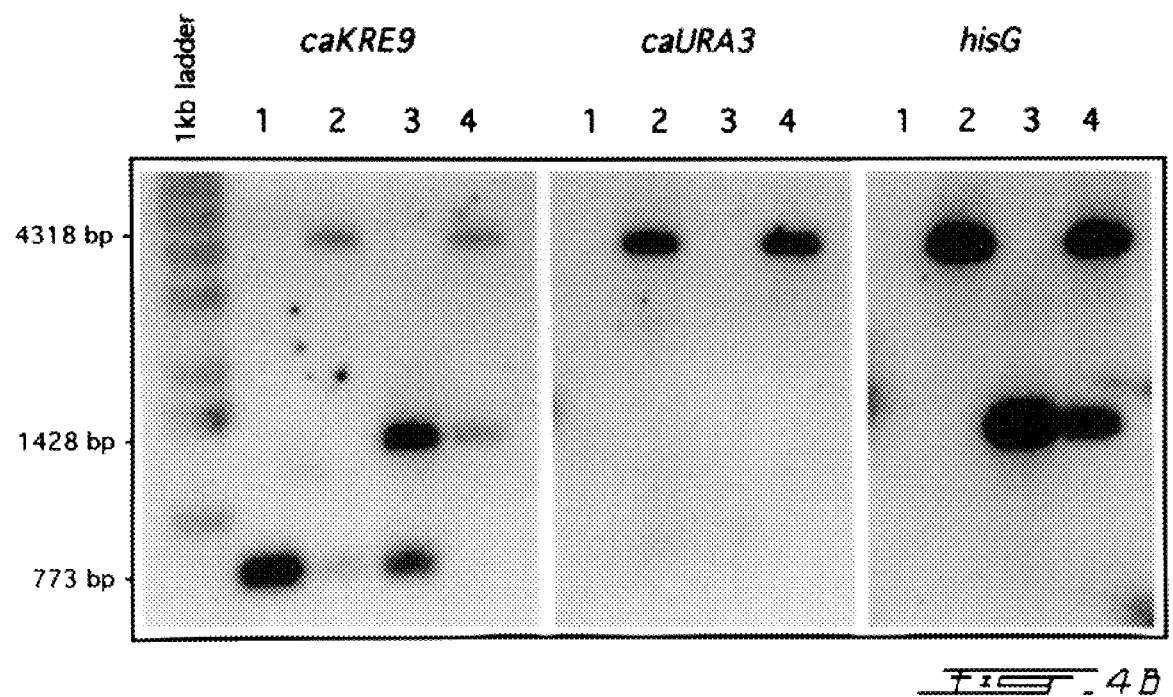
FIG. 4B illustrates the Southern blot verification of the correct integration of the hisG-URA3-hisG disruption module into the CaKRE9 gene and proper CaURA3 excision after 5-FOA treatment.
Figure 9:
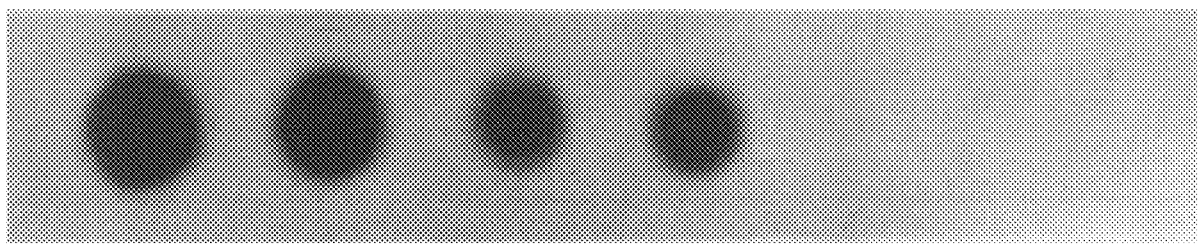

In accordance with the present invention, the synthesis and the assembly of the cell wall polymer β1,6 glucan which plays a central role in the organization of the yeast cell wall and which is indispensable for cell viability were extensively studied. Although the biochemistry of β1,6 glucosylation is incompletely understood, a genetic analysis of genes required for 1,6 synthesis has been performed in *Saccharomyces cerevisiae*, and has identified many genes required for this process. These encode products acting in the endoplasmic reticulum, the Golgi complex and at the cell surface.

In accordance with the present invention a novel gene was identified, KRE9, whose product is required for the synthesis of β1,6 linked glucans (Brown J L. et al. (1993) *Molecular & Cellular Biology* 13:6346–6356). KRE9 appears to be a fungal specific gene, as it is absent from animal lineages based on data base searches of the *Caernorhabditis elegans*, mouse and *Homo sapiens* genomes and it also appears to be absent from the plant, bacterial and archaebacterial lineages.

KRE9 and its Homolog KNH1

KRE9 encodes a 30-kDa secretory pathway protein involved in the synthesis of cell wall β1,6 glucan (Brown J L. et al. (1993) *Molecular & Cellular Biology* 13:6346–6356). Disruption of KRE9 in *S. cerevisiae* leads to serious growth impairment and an altered cell wall containing less than 20% of the wild-type amount of β1,6 glucan. Analysis of the glucan material remaining in a kre9 null mutant indicated a polymer with a reduced average molecular mass (Brown J L. et al. (1993) *Molecular & Cellular Biology* 13:6346–6356). The kre9 null mutants also displayed several additional cell-wall-related phenotypes, including an aberrant multiple budded morphology, a mating defect, and a failure to form projections in the presence of alpha-factor. Antibodies generated against Kre9p detected an O-glycoprotein of approximately 55 to 60 kDa found in the extracellular medium of a strain overproducing Kre9p, indicating it is normally localized at the cell surface.

In the yeast genome a KRE9 homolog was recently found, KNH1, whose product, Knh1p, shares 46% overall identity with Kre9p (Dijkgraaf G J. et al. (1996) *Yeast* 12:683–692). Disruption of the KNH1 locus has no effect on growth, killer toxin sensitivity or β1,6-glucan levels. Overexpression of KNH1 suppressed the severe growth defect of a kre9 null mutant and restored the level of alkali-insoluble β1,6-glucan to almost wild type levels. When overproduced, Knh1p, like Kre9p, can be found in the extracellular culture medium as an O-glycoprotein, and is likely also a cell surface protein under conditions of normal expression. The disruption of both KNH1 and KRE9 is lethal. Transcription of KNH1 is carbon-source and KPE9 dependent. The severe growth defect of a kre9Δ null mutant observed on glucose can be partially restored when galactose becomes the major carbon source. Transcription of the KNH1 gene is normally low in wild type cells grown on glucose but increases approximately five fold in galactose grown cells, where it partially compensates for the loss of Kre9p and allows partial suppression of the slow growth phenotype of kre9Δ cells. These results 25 suggest that KRE9 and KNH1 are specialized in vivo to function under different environmental conditions (Dijkgraaf G J. et al. (1996) *Yeast* 12:683–692).

The essential nature of the KRE9/KNH1 gene pair, and the putative extracellular location of their gene products make these proteins a new and potentially valuable target for antifungal compounds that need not enter the fungal cell.

β1,6-glucan in Pathogenic Fungi

The yeast *Saccharomyces cerevisiae*, although not a pathogen, is a proven model organism for pathogenic fungi as it is closely related taxonomically to opportunistic pathogens like the dimorphic yeast *Candida albicans*. The composition of the cell wall of *C. albicans* resembles that of *S. cerevisiae* in containing β1,3- and β1,6-glucans, chitin, and mannoproteins (Mio, T. et al., *J. Bacteriol.* 179:2363–2372 Analyses of the *Candida albicans* genes involved in extracellular matrix assembly are limited but indicate that the proteins responsible for synthesis of the polymers often resemble those found in the more extensively studied yeast, *Saccharomyces cerevisiae*. The β1,6 glucosylation of proteins appears to be widespread among fungal groups, and the polymer varies in abundance between fungal species. In *C. albicans* this polymer is particularly abundant, comprising approximately half of the alkali insoluble glucan. Comparative studies with *C. albicans* have so far identified three genes involved in β1,6 =glucosylation based on their relatedness to those in *S. cerevisiae*, indicating that synthesis of this polymer is functionally conserved and essential for the growth of *Candida albicans*.

Isolation of the CaKRE9 Gene

In order to validate KRE9 as a possible new antifungal target, we have examined if genes related to *S. cerevisiae* KRE9 were present in *C. albicans*. Using complementation of the *S. cerevisiae* kre9 mutant phenotype as a screen, we have isolated a *C. albicans* gene that encodes a protein similar to the *S. cerevisiae* KRE9 gene product.

CaKRE9 was identified by a plasmid shuffle approach as a gene being able to restore the slow growth of a *Saccharomyces cerevisiae* kre9::HIS3 disrupted strain. A diploid strain heterozygous for a kre9::HIS3 deletion was transformed with a centromeric LYS2-based pRS317 vector containing a wild type copy of the *S. cerevisiae* KRE9 gene. Transformants were selected by prototrophic growth on minimal media, sporulated and a haploid kre9::HIS3 strain containing a plasmid-based copy of KRE9 was obtained by tetrad dissection and spore progeny analysis. This strain was shown to possess wild type growth and killer toxin sensitivity and was subsequently transformed with a *Candida albicans* genomic library contained within the multicopy YEp352-plasmid harboring the URA3 gene as a selectable marker. In order to screen for plasmids that could restore growth to a kre9::HIS3 mutant, about 20,000 His3$^+$ Lys2$^+$ Ura3$^+$ cells were replica plated on minimal medium containing α-aminoadipate as a primary nitrogen source to select for cells that have lost the LYS2 plasmid-based copy of KRE9 but are still able to grow, indicating that a copy of the complementing CaKRE9 gene could be present in such growing cells. These cells were further tested for loss of the pRS317-KRE9 plasmid by failure to grow on medium lacking lysine. YEp352-based *Candida albicans* genomic DNA was recovered from cells that grew in the presence of lysine but did not grow in its absence. Upon retransformation in yeast, only 2 different genomic inserts were able to partially restore growth of the kre9::HIS3 haploid strain. DNA from both inserts were sequenced.

The CaKRE9 gene was contained in only one of the *C. albicans* clones. Complete sequencing of the 8-kb fragment containing the CaKRE9 gene revealed an open reading frame of 813 bp encoding a 29-kDA secretory protein of 271 amino acid residues (see FIG. 1). As is the case with Kre9p and Knh1p (Brown J L. et al. (1993) *Molecular & Cellular Biology* 13:6346–6356; Dijkgraaf G J. et al. (1996) *Yeast* 12:683–692), the hydrophobic N-terminal region of CaKre9p comprises an eukaryotic signal sequence, with the most likely cleavage site occurring between amino acid residues 21 and 22. CaKre9p shares 43% overall identity with Kre9p and 32% with Knh1p (see FIG. 2). The amino acid residues are shown in single-letter amino acid code. Sequences were aligned with gaps to maximize homology. Dots represent a perfect match between all sequences while a vertical slash indicates conservative substitution at a given position. The most conserved region between the 3 proteins encompasses a large part of the central region and most of the C-terminal portion, with the N-terminal part being largely unique to each protein. Kre9p, Knh1p and CaKre9p share a high proportion of serine and threonine residues (26%), potential sites for O-glycosylation, a modification known to occur on Kre9p and Knh1p, and characteristic of many yeast cell surface proteins. In addition, all 3 proteins have lysine and arginine rich C-termini and lack potential N-linked glycosylation sites.

The functional capacity of CaKre9p was assessed in *Saccharomyces cerevisiae* by measuring its ability to restore the growth and killer toxin sensitivity of a kre9 null mutant. Firstly, the YEp352-based *Candida albicans* genomic DNA containing the CaKRE9 gene was transformed into a diploid strain of *S. cerevisiae* heterozygous for a kre9::HIS3 deletion, sporulated and a haploid kre9::HIS3 strain containing a plasmid-based copy of CaKRE9 was obtained from spore progeny following tetrad dissection. As can be seen in FIG. 3A, a strain harboring the CaKRE9 gene grows at a slower rate than a wild type strain or the mutant strain harboring a copy of KRE9 but significantly faster than the kre9 null mutant which has a severe growth phenotype. Secondly, the haploid kre9 strain carrying the CaKRE9 was submitted to a killer toxin sensitivity assay (FIG. 3B). K1 killer yeast strains secrete a small poreforming toxin that requires an intact cell wall receptor for function. KRE9 null mutations lead to a considerable decrease in the level of β1,6-glucan disrupting the toxin receptor (Brown J L. et al. (1993) *Molecular & Cellular Biology* 13:6346–6356), leading to killer resistance and showing no killing zone in the assay. The killer phenotype of the kre9 mutant allowed a test of possible suppression by CaKre9p. Overexpression of CaKRE9 in the *S. cerevisiae* haploid strain carrying a disrupted copy of KRE9 partially suppressed the killer resistance phenotype (FIG. 3B).

These results imply that Kre9p and CaKre9p both play very similar roles in β1,6-glucan assembly in *S. cerevisiae* and *C. albicans*.

Disruption of the CaKRE9 Gene

Experimental Strategy:

The gene disruption was performed by the URA blaster protocol using the hisG-CaURA3-hisG module. A 1.6-kb DraI DNA fragment containing the CaKRE9 gene was subcloned from the original insert into the SmaI site and the blunted XbaI site (treated with the Klenow fragment of DNA polymerase I) of YEp352 (see FIG. 4A) Extracted genomic DNAs are from: CAI4 wild type cells (lane 1), CaKRE9/Cakre9::hisG-URA-hisG heterozygous mutant (lane 2), CaKRE9/Cakre9::hisG heterozygous mutant obtained after 5-FOA treatment (lane 3) and Cakre9/Cakre9::hisG-URA-hisG homozygous null mutant which is able to grow only when galactose is used as the sole source of carbon.

The CaKRE9 gene was disrupted by deleting a 485 bp BstxI-BamHI fragment of the open reading frame and replacing it by a 4.0 kb BglII/BamHI fragment carrying the hisG-URA3-hisG module from plasmid pCUB-6 (see FIG. 4A). The sticky ends were enzymatically treated to accommodate the ligation. This disruption plasmid was digested by HindIII and KpnI, precipitated with ethanol and sodium acetate and 100 μg of the 5.2 kb-disruption fragment was transformed into CAI4 *Candida albicans* cells by the lithium acetate method.

Putative heterozygous disruptants were selected on minimal medium carrying glucose or galactose as carbon sources but lacking uracil. In preparation for a second round of gene disruption, the CaURA gene was excised using a 5-FOA selection. The second round of transformation was performed in the same way as the primary one.

The accurate integration of the hisG-CaURA3-hisG cassette into the CaKRE9 gene and its excision from genomic DNA was verified by Southern hybridization using 3 different probes:

(1) a 405-bp fragment from *C. albicans* genomic DNA containing coding and 31 flanking sequences of CaKRE9;

(2) a 783 bp DNA fragment obtained by PCR and covering the entire CaURA3 coding region; and (3) a 898 bp fragment amplified by PCR that encompasses the whole of the *Salmonella typhimurium* hisG gene (see FIG. 4B).

All genomic DNAs were digested with the BamHI and SalI restriction enzymes.

Results:

In the first round of transformation where transformants were selected on glucose containing plates, the Southern blotting results revealed that the hisG-CaURA3-hisG module correctly integrated into the *Candida albicans* KRE9 gene (see FIG. 4). When genomic DNA of putative heterozygous CaKRE9 disruptions was digested with the SalI and BamHI restriction enzymes and probed with the CaKRE9 405-bp SalI-BstXI DNA fragment along with the hisG and the CaURA3 probes, 2 expected bands could be detected (see FIG. 4B, lane 2, for representative result): a 773 bp band corresponding to the wild type gene that could only be detected by the CaKRE9 probe and a 4318 bp diagnostic band, revealed by all 3 probes, indicating successful disruption of one copy of the CaKRE9 gene. After removal of the CaURA3 using 5-FOA, the 773 bp wild type band could still be visualized but the disrupted band from which the CaURA3 was excised shifted to an anticipated 1428 bp when probed with the CaKRE9 and hisG probes but not with the CaURA3 probe (see FIG. 4B, lane 3).

In order to assess if the CaKRE9 gene is essential in *C. albicans*, a second round of disruptions was undertaken in the heterozygous strain where the CaURA3 gene was eliminated. However, in view of the nature of the carbon source regulation of the KRE9/KNH1 pair in *S. cerevisiae*, the second round of transformation was executed using both glucose and galactose as carbon sources. 32 Ura$^+$ colonies from the glucose plated transformation were analyzed by Southern blot hybridization using the 3 different probes and only yeast cells heterozygous at the CaKRE9 locus could be found. The absence of the expected homozygous double disruption among the transformants is consistent with the fact that CaKRE9 is an essential gene in *C. albicans* when glucose is the sole carbon source. Demonstration of CaKRE9 as an essential gene under these conditions validates the CaKRE9 gene product as a therapeutic target in *Candida albicans*.

The population of transformants growing on galactose was heterogeneous with large and small sized colonies occurring. As a first assessment of a possible carbon source dependence, a total of 26 colonies of different sizes were plated from galactose to glucose. Among the smaller ones, 8 did not grow on glucose, suggesting that they could be homozygous disruptants. Southern blot hybridizations were performed on these 8 transformants and they were shown to be homozygous disruptants for the CaKRE9 locus: one copy corresponded to the disrupted gene in which CaURA3 has been removed (1428 bp) and the second one represented the inactivation of the remaining wild type copy by the hisG-caURA3-hisG module (4318 bp; FIG. 4B, lane 4). Thus a homozygous disruption of kre9 in *C. albicans* is lethal when glucose constitutes the exclusive carbon source. Further, it should be appreciated that glucose is the main source of carbon of human beings.

β1,6-Glucan Analysis of *C. albicans* CaKRE9 Mutants

Experimental Strategy:

Yeast total-cell protein extracts were prepared from exponentially growing cultures by cell lysis with glass beads. Cellular extracts were standardized for total cellular protein and equivalent amounts of protein were alkali extracted (0.75M NaOH final 1 h, 75° C.). The alkali soluble fractions were then spotted onto nitrocellulose and immunoblots were carried out. Briefly, blots were treated in TBST buffer (10 mM Tris pH 8.0, 150 mM NaCl, 0.05% Tween™ 20, containing 5% non fat dried milk powder) and subsequently incubated with 25 affinity purified rabbit anti-β1,6-glucans antibodies (prepared as described Montijn, R. C. et al. (1994) *J. Biol. Chem.* 296:19338–19342) in the same buffer. After antibody binding, membranes were washed in TBST and a second antibody directed against rabbit immunoglobulins and conjugated with horseradish peroxidase, was then added. The blots were again washed and whole cell β1,6 glucans detected using an enhanced chemiluminescence procedure.

Results

In order to directly measure the effect of inactivating CaKRE9 on β1,6-glucan synthesis and assembly, a specific rabbit anti-β1,6-glucan antiserum was raised against BSA-coupled pustulan (a commercially available β1,6 glucan), affinity purified, and used to detect antigen-antibody complexes by Western blotting of total cell protein extracts of different yeast strains grown on galactose. As expected, wild type cells yielded a strong β1,6-glucan signal (see FIG. 5). The affinity purified Ab detected about a quarter of the glucan in the *C. albicans* heterozygous Δcakre9 whereas no β1,6-glucan could be detected from a *C. albicans* homozygous Δcakre9 disruptant grown on galactose (FIG. 5).

Discussion

The essential nature of the KRE9 gene in *C. albicans*, and the possible extracellular location of its gene product make this protein a new and potentially valuable target for antifungal compounds that need not enter the fungal cell. The precise role of Kre9p in β-glucan synthesis remains to be precisely determined but does not prevent the establishment of a antifungal drug screening assay.

The present invention will be more readily understood by referring to the following examples which are given to illustrate the invention rather than to limit its scope.

EXAMPLE I

In Vitro Screening Method for Specific Antifungal Agents (Enzymatic-Based Assay)

The primary objective is to identify novel compounds inhibiting the synthesis, assembly and/or regulation of β1,6-glucans. This enzymatic assay would utilize some of the gene products (KRE) involved in β1,6-glucan synthesis, including using an in vitro assay for CaKre9p. Using specific reagents such as an antibody to β1,6-glucan, and a specific glucanase for the polymer, the approach is to synthesize the polymer in vitro from the activated sugar monomer UDP-glucose. This task can be accomplished by existing methodologies such as the production of large amounts of each protein and by the availability of genetic tools, such as the ability to delete or overexpress gene products that are involved in synthesis of this and the other major polymers. Once the assay has been established it will permit the screening of possible compounds that inhibit steps in the synthesis of this essential polymer. When such inhibitors will be found, they will then be evaluated as candidates for specific antifungal agents.

The effects of such compounds on β1,6-glucan levels may be directly measured using the anti-β1,6-glucan antibody. This approach can be used on all type of fungi and can be adapted to a high throughput immunoassay to find β1,6-glucan inhibitors.

EXAMPLE II

In Vivo Screening Method for Specific Antifungal Agents (Cellular-Based Assay)

Yeast strains possessing or lacking β1,6-glucans permit a differential screen for compounds inhibiting synthesis of this cell wall polymer. Specifically, an antifungal drug screen can be devised based on a wholecell assay in which the fungal-specific CaKre9p would be targeted.

The strains that may be used in accordance with the present invention include, without limitation, any yeast strain mutant for CaKRE9 and homologs thereof disrupted strain, conditional mutants, overexpression strains and suppressed disrupted strains.

Compounds can be tested for their ability to inhibit growth or kill a wild type *C. albicans* strain while having no effect on a Cakre9 suppressor strain. In addition, compounds leading to hypersensitivity in a CaKRE9 deletion will also be of value as candidate antifungal drugs. The finding of new antifungal compounds will be greatly simplified by these types of screens. The direct scoring on cells of the level of efficacy of a particular compound (natural product extracts, pure chemicals . . . ) alleviates the costly and labor intensive establishment of an in vitro enzymatic assay. The availability of genetic tools, such as the ability to delete or overexpress gene products that are involved in synthesis of this and the other major polymers will permit the establishment of this new screening method. When such inhibitors will be found, they will then be evaluated as candidates for specific antifungal agents.

EXAMPLE III

The use of CaKRE9 in the Diagnosis of Fungal Infection

Detection Based on PCR

Candida spp. and other pathogenic fungi are traditionally identified by morphological and metabolic characteristics and often this require days to weeks to isolate on culture from a patient's sample. Identification is time-consuming and often unreliable and this impedes the selection of antimicrobial agents in cases in which species identification of the organism is necessary. Moreover, culture-based diagnostic methods are not within the scope of many routine microbiology laboratories and are frequently limited to detection of pathogenic organisms in patients at an advanced stage of disease or even at autopsy. The detection of disseminated Candida mycosis is an area where there is an urgency for new sophisticated techniques of identification. Polymerase Chain Reaction (PCR) based tests to establish the presence of a fungal infection are at this point highly desirable for laboratory diagnosis and management of patients with serious fungal diseases. The CaKRE9 gene is fungi specific and could be used to develop new diagnostic procedures of mycosis based on the PCR. Such diagnostic tests would be predicted to be highly sensitive and specific. Ultimately, simple kits permitting the diagnosis of fungal infections will be sold to hospitals and specialized clinics. Current trends in the hospital microbiology laboratories indicate that there will be a considerable future increase in use of the PCR as a diagnostic tool.

Detection Based on Anti-CaKre9p Antibodies

CaKre9p is thought to be localized at the cell surface and as such could be detected as a circulating candidal antigen by an enzyme-linked immunoabsorbent assay (ELISA) detection kit based on antibodies directed against CaKre9p. Antibodies directed against CaKre9p could allow levels of specificity and sensitivity high enough to permit commercialization of a diagnostic kit.

EXAMPLE IV

The use of Kre9p in all Fungi

Isolation and use of functional homologs of KRE9/CaKRE9 from all fungi. Most fungi have β1,6-glucans and likely have KRE9 homologs in their genome. The kre9 mutant can allow isolation of similar genes by functional complementation from other pathogenic fungi as what was done to isolate CaKRE9. KRE9 could also serve as a probe to isolate by homology KRE9 homologs from other yeasts. In addition, Kre9p allows isolation of homologs in other species by the techniques of reverse genetics where antibodies raised against Kre9p could be used to screen expression libraries of pathogenic fungi for expression of KRE9 homologs that would immunologically cross react with antibodies raised against *S. cerevisiae* KRE9 and *C. albicans* CaKRE9. These putative KRE9 homologs in these pathogenic fungi could serve as targets for potential new antifungals.

Other methods are used to find proteins which interact with Kre9p and homologs thereof, such as two-hybrid, co-immunoprecipitation and chromatography using an activated Kre9p matrix.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated nucleic acid molecule, comprising the nucleotide sequence as set forth in SEQ. ID. NO: 1, encoding a gene product essential for cell wall glucan synthesis of *Candida albicans*.

2. An isolated nucleic acid molecule, comprising the nucleotide sequence encoding, amino acid sequence set forth in SEQ ID NO 2.

3. The isolated nucleic acid molecule of claim 2, wherein the nucleic acid is DNA.

4. The isolated nucleic acid molecule of claim 2, wherein the nucleic acid is RNA.

5. The isolated nucleic acid molecule of claim 3, wherein the nucleic acid molecule comprises the nucleic acid sequence as set forth in SEQ ID NO 1.

6. An antifungal screening assay for identifying a compound which inhibits the synthesis, assembly and/or regulation of *Candida albicans* β1,6-glucan through the nucleic acid molecule of claim 1, which comprises the steps of:
   a) synthesizing β1,6-glucan in vitro from activated sugar monomer/polymer and specific β1,6-glucan synthetic proteins containing at least CaKre9;
   b) subjecting step a) to a high throughput compound screen determining concentration of said β1,6-glucan synthesized, wherein reduction in β1,6-glucan concentration is indicative of an antifungal compound.

7. The antifungal screening assay of claim 6, wherein the activated sugar monomer/polymer is isolated from *Candida albicans*.

8. The antifungal screening assay of claim 6, wherein the specific β-1,6glucan synthetic proteins comprise a glucanase.

9. The antifungal screening assay of claim 6, wherein the specific β-1,6-glucan synthetic proteins are isolated from *Candida albicans*.

10. The antifungal screening assay of claim 9, wherein one of the specific specific β-1,6-glucan synthetic proteins is CaKre9p.

11. The antifungal screening assay of claim 10, wherein the CaKre9p comprises the amino acid sequence set forth in SEQ ID NO 2.

12. The antifungal screening assay of claim 6, wherein the compound that inhibits the synthesis, assembly and/or regulation of β-1,6-glucan inhibits CaKRE9p activity.

13. The antifungal screening assay of claim 6, wherein the determining concentration of β-1,6-glucan is achieved by directly measuring β-1,6-glucan using an anti-β-1,6-glucan antibody.

* * * * *

SEQUENCE LISTING

<160> NUMBER OF SEQ ID NOS: 4

<210> SEQ ID NO 1
<211> LENGTH: 816
<212> TYPE: DNA
<213> ORGANISM: Candida albicans CaKRE9

<400> SEQUENCE: 1

```
atgagacaat ttcaaatcat attaatttcc cttgttgttt ccataataag atgtgttgtt      60
gcagatgttg acatcacatc accaaagagt ggagaaactt tttctggtag ttctggatca     120
```

-continued

```
gcaagtatca agattacctg ggatgattca gacgattcag actcaccgaa atctttggat    180
aatgccaaag ggtacacaat ttctttatgt actggaccta cttcagatgg ggatatccag    240
tgtttggatc cattagtcaa gaacgaagct attgcaggta aatctaaaac agtttctatt    300
ccccagaact cagtacctaa tggttattac tatttccaaa tttacgttac tttcactaat    360
ggaggtacca ctattcatta ttcaccacgt ttcaaattga ctggtatgtc tggtccaact    420
gccactttag atgtcaccga aacaggatcg gtgccagcgg atcaagcttc aggatttgat    480
actgcaacta ctgccgactc caaatctttc acagttccat atccctaca aacagggaag    540 accagatacg caccaatgca aatgcaacca ggtaccaaag tgactgctac aacctggagt    600
atgaagttcc caactagtgc tgttacttac tactcaacaa aggctggcac accaaatgtg    660
gcctctacta ttaccccagg ttggagttat actgctgaat ctgccgttaa ctatgctagt    720
gttgctccat atccaacata ctggtatcct gccagtgaac gagtgagtaa ggctacaatt    780
agtgctgcta caaagagaag aagatggttg gattga                              816
```

<210> SEQ ID NO 2
<211> LENGTH: 271
<212> TYPE: PRT
<213> ORGANISM: Candida albicans CaKRE9

<400> SEQUENCE: 2

```
Met Arg Gln Phe Gln Ile Ile Leu Ile Ser Leu Val Val Ser Ile Ile
  1               5                  10                  15

Arg Cys Val Val Ala Asp Val Asp Ile Thr Ser Pro Lys Ser Gly Glu
             20                  25                  30

Thr Phe Ser Gly Ser Ser Gly Ser Ala Ser Ile Lys Ile Thr Trp Asp
         35                  40                  45

Asp Ser Asp Ser Asp Ser Pro Lys Ser Leu Asp Asn Ala Lys Gly
     50                  55                  60

Tyr Thr Ile Ser Leu Cys Thr Gly Pro Thr Ser Asp Gly Asp Ile Gln
 65                  70                  75                  80

Cys Leu Asp Pro Leu Val Lys Asn Glu Ala Ile Ala Gly Lys Ser Lys
                 85                  90                  95

Thr Val Ser Ile Pro Gln Asn Ser Val Pro Asn Gly Tyr Tyr Tyr Phe
            100                 105                 110

Gln Ile Tyr Val Thr Phe Thr Asn Gly Gly Thr Thr Ile His Tyr Ser
        115                 120                 125

Pro Arg Phe Lys Leu Thr Gly Met Ser Gly Pro Thr Ala Thr Leu Asp
    130                 135                 140

Val Thr Glu Thr Gly Ser Val Pro Ala Asp Gln Ala Ser Gly Phe Asp
145                 150                 155                 160

Thr Ala Thr Thr Ala Asp Ser Lys Ser Phe Thr Val Pro Tyr Thr Leu
                165                 170                 175

Gln Thr Gly Lys Thr Arg Tyr Ala Pro Met Gln Met Gln Pro Gly Thr
            180                 185                 190

Lys Val Thr Ala Thr Trp Ser Met Lys Phe Pro Thr Ser Ala Val
        195                 200                 205

Thr Tyr Tyr Ser Thr Lys Ala Gly Thr Pro Asn Val Ala Ser Thr Ile
    210                 215                 220

Thr Pro Gly Trp Ser Tyr Thr Ala Glu Ser Ala Val Asn Tyr Ala Ser
225                 230                 235                 240

Val Ala Pro Tyr Pro Thr Tyr Trp Tyr Pro Ala Ser Glu Arg Val Ser
```

```
                        245                 250                 255
Lys Ala Thr Ile Ser Ala Ala Thr Lys Arg Arg Trp Leu Asp
                260                 265                 270

<210> SEQ ID NO 3
<211> LENGTH: 276
<212> TYPE: PRT
<213> ORGANISM: Saccharomyces cerevisiae Kre9P

<400> SEQUENCE: 3

Met Arg Leu Gln Arg Asn Ser Ile Ile Cys Ala Leu Val Phe Leu Val
  1               5                  10                  15

Ser Phe Val Leu Gly Asp Val Asn Ile Val Ser Pro Ser Ser Lys Ala
                 20                  25                  30

Thr Phe Ser Pro Ser Gly Gly Thr Val Ser Val Pro Val Glu Trp Met
             35                  40                  45

Asp Asn Gly Ala Tyr Pro Ser Leu Ser Lys Ile Ser Thr Phe Thr Phe
         50                  55                  60

Ser Leu Cys Thr Gly Pro Asn Asn Ile Asp Cys Val Ala Val Leu
 65                  70                  75                  80

Ala Ser Lys Ile Thr Pro Ser Glu Leu Thr Gln Asp Asp Lys Val Tyr
                 85                  90                  95

Ser Tyr Thr Ala Glu Phe Ala Ser Thr Leu Thr Gly Asn Gly Gln Tyr
            100                 105                 110

Tyr Ile Gln Val Phe Ala Gln Val Asp Gly Gln Gly Tyr Thr Ile His
        115                 120                 125

Tyr Thr Pro Arg Phe Gln Leu Thr Ser Met Gly Gly Val Thr Ala Tyr
    130                 135                 140

Thr Tyr Ser Ala Thr Thr Glu Pro Thr Pro Gln Thr Ser Ile Gln Thr
145                 150                 155                 160

Thr Thr Thr Asn Asn Ala Gln Ala Thr Thr Ile Asp Ser Arg Ser Phe
                165                 170                 175

Thr Val Pro Tyr Thr Lys Gln Thr Gly Thr Ser Arg Phe Ala Pro Met
            180                 185                 190

Gln Met Gln Pro Asn Thr Lys Val Thr Ala Thr Thr Trp Thr Arg Lys
        195                 200                 205

Phe Ala Thr Ser Ala Val Thr Tyr Tyr Ser Thr Phe Gly Ser Leu Pro
    210                 215                 220

Glu Gln Ala Thr Thr Ile Thr Pro Gly Trp Ser Tyr Thr Ile Ser Ser
225                 230                 235                 240

Gly Val Asn Tyr Ala Thr Pro Ala Ser Met Pro Ser Asp Asn Gly Gly
                245                 250                 255

Trp Tyr Lys Pro Ser Lys Arg Leu Ser Leu Ser Ala Arg Lys Ile Asn
            260                 265                 270

Met Arg Lys Val
        275

<210> SEQ ID NO 4
<211> LENGTH: 267
<212> TYPE: PRT
<213> ORGANISM: Saccharamyces cerevisiae Knh1p

<400> SEQUENCE: 4

Met Leu Ile Val Leu Phe Leu Thr Leu Phe Cys Ser Val Val Phe Arg
  1               5                  10                  15

Thr Ala Tyr Cys Asp Val Ala Ile Val Ala Pro Glu Pro Asn Ser Val
```

-continued

```
                     20                  25                  30
Tyr Asp Leu Ser Gly Thr Ser Gln Ala Val Val Lys Val Lys Trp Met
            35                  40                  45
His Thr Asp Asn Thr Pro Gln Glu Lys Asp Phe Val Arg Tyr Thr Phe
     50                  55                  60
Thr Leu Cys Ser Gly Thr Asn Ala Met Ile Glu Ala Met Ala Thr Leu
 65                  70                  75                  80
Gln Thr Leu Ser Ala Ser Asp Leu Thr Asp Asn Glu Phe Asn Ala Ile
                 85                  90                  95
Ile Glu Asn Thr Val Gly Thr Asp Gly Val Tyr Phe Ile Gln Val Phe
             100                 105                 110
Ala Gln Thr Ala Ile Gly Tyr Thr Ile His Tyr Thr Asn Arg Phe Lys
         115                 120                 125
Leu Lys Gly Met Ile Gly Thr Lys Ala Ala Asn Pro Ser Met Ile Thr
     130                 135                 140
Ile Ala Pro Glu Ala Gln Thr Arg Ile Thr Thr Gly Asp Val Gly Ala
145                 150                 155                 160
Thr Ile Asp Ser Lys Ser Phe Thr Val Pro Tyr Asn Leu Gln Thr Gly
                165                 170                 175
Val Val Lys Tyr Ala Pro Met Gln Leu Gln Pro Ala Thr Lys Val Thr
            180                 185                 190
Ala Lys Thr Trp Lys Arg Lys Tyr Ala Thr Ser Glu Val Thr Tyr Tyr
        195                 200                 205
Tyr Thr Leu Arg Asn Ser Val Asp Gln His Thr Thr Val Thr Pro Gly
    210                 215                 220
Trp Ser Tyr Ile Ile Thr Ala Asp Ser Asn Tyr Ala Thr Ala Pro Met
225                 230                 235                 240
Pro Ala Asp Asn Gly Gly Trp Tyr Asn Pro Arg Lys Arg Leu Ser Leu
                245                 250                 255
Thr Ala Arg Lys Val Asn Ala Leu Arg His Arg
                260                 265
```